United States Patent
Corradini et al.

(10) Patent No.: US 8,378,159 B2
(45) Date of Patent: Feb. 19, 2013

(54) PROCESS AND SYSTEM FOR CONVERTING BIOGAS TO LIQUID FUELS

(75) Inventors: Andrew Corradini, Foster City, CA (US); Jarod McCormick, Menlo Park, CA (US)

(73) Assignee: Oberon Fuels, Inc., La Jolla, CA (US)

(\*) Notice: Subject to any disclaimer, the term of this patent is extended or adjusted under 35 U.S.C. 154(b) by 0 days.

(21) Appl. No.: 13/133,380

(22) PCT Filed: Dec. 17, 2009

(86) PCT No.: PCT/US2009/068477
§ 371 (c)(1),
(2), (4) Date: Oct. 13, 2011

(87) PCT Pub. No.: WO2010/078035
PCT Pub. Date: Jul. 8, 2010

(65) Prior Publication Data
US 2012/0022306 A1    Jan. 26, 2012

Related U.S. Application Data

(60) Provisional application No. 61/138,350, filed on Dec. 17, 2008.

(51) Int. Cl.
*C07C 15/42* (2006.01)

(52) U.S. Cl. .......... 585/14; 585/7; 585/24; 585/469; 585/638; 585/369; 585/640; 585/700; 585/733; 585/903; 423/651; 423/652; 423/653; 423/654

(58) Field of Classification Search .......... 423/651–654; 252/373; 585/469, 638–640, 700, 733, 903
See application file for complete search history.

(56) References Cited

U.S. PATENT DOCUMENTS

| | | | |
|---|---|---|---|
| 3,929,431 A * | 12/1975 | Koh et al. ............... | 48/214 R |
| 3,998,930 A | 12/1976 | McArthur | |
| 4,031,123 A | 6/1977 | Espino et al. | |
| 4,423,155 A | 12/1983 | Bell et al. | |
| 4,567,204 A | 1/1986 | Mednick et al. | |
| 4,590,176 A | 5/1986 | Hoek et al. | |
| 4,628,066 A | 12/1986 | Bonnell et al. | |
| 5,218,003 A | 6/1993 | Lewnard et al. | |
| 5,254,520 A * | 10/1993 | Sofianos ................ | 502/307 |
| 5,753,716 A | 5/1998 | Peng et al. | |
| 6,504,072 B1 * | 1/2003 | Brown et al. ............ | 585/467 |

(Continued)

OTHER PUBLICATIONS

Hessel, et al.; Review on Patents in Microreactor and Micro Process Engineering; Recent Patents on Chemical Engineering (2008), 1, 1-16.

(Continued)

*Primary Examiner* — Brian McCaig
(74) *Attorney, Agent, or Firm* — Knobbe Martens Olson & Bear LLP

(57) ABSTRACT

A method of producing a hydrocarbon fuel from a hydrocarbon-containing gas is disclosed and described. A hydrocarbon-containing gas is produced (10) containing from about 25% to about 50% carbon dioxide and can be reformed (12) with a steam gas to form a mixture of hydrogen, carbon monoxide and carbon dioxide. The reforming can be a composite dry-wet reforming or a tri-reforming step. The mixture of hydrogen, carbon monoxide and carbon dioxide can be at least partially converted (14) to a methanol product. The methanol product can be converted to the hydrocarbon fuel (18), optionally via DME synthesis (16). The method allows for effective fuel production with low catalyst fouling rates and for operation in an unmanned, self-contained unit at the source of the hydrocarbon-producing gas.

14 Claims, 1 Drawing Sheet

U.S. PATENT DOCUMENTS

| | | | |
|---|---|---|---|
| 6,758,101 | B2 | 7/2004 | Valentine |
| 2003/0111410 | A1 | 6/2003 | Branson |
| 2006/0020155 | A1 | 1/2006 | Beech et al. |
| 2007/0036707 | A1 | 2/2007 | Betta et al. |
| 2007/0238610 | A1* | 10/2007 | Chen et al. .................. 502/330 |
| 2008/0021251 | A1* | 1/2008 | Iaccino et al. ............... 585/316 |
| 2008/0260628 | A1 | 10/2008 | Moon et al. |
| 2008/0319245 | A1* | 12/2008 | Fujimoto et al. ............. 585/733 |

OTHER PUBLICATIONS

Packer; The Production of Methanol and Gasoline, available at: http://nzic.org/nz/ChemProcesses/energy.

Pan, et al.; Catalytic Tri-reforming of Methane Using Flue Gas from Fossil Fuel-based Power Plants; Fuel Chemistry Division Preprints (2002), 47(1), 262-264.

Tonkovich, et al.; The catalytic partial oxidation of methane in a microchannel chemical reactor; in: W. Ehrfeld, I.-H. Rinard, R.S. Wegeng (Eds.), 2nd International Conference on Microreaction Technology (IMRET 2), AIChE, New Orleans, 1998, p. 45.

PCT/US2010/027681 International Search Report dated Sep. 20, 2011.

PCT/US2009/068477 International Search Report dated Aug. 9, 2010.

* cited by examiner

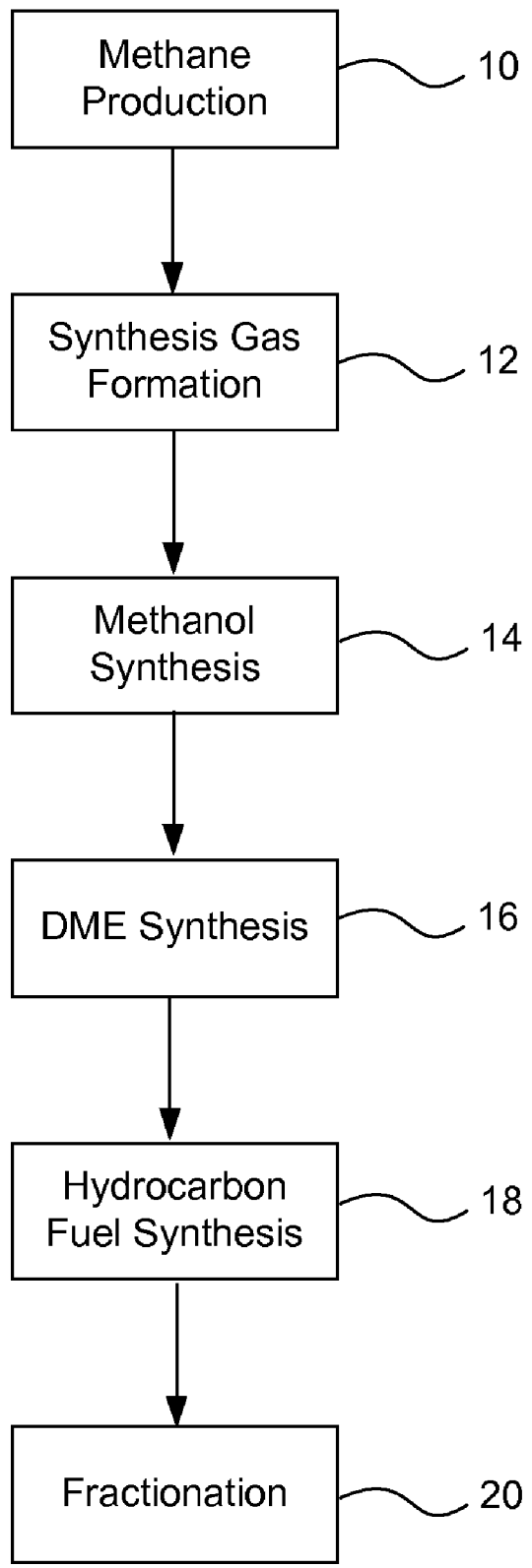

PROCESS AND SYSTEM FOR CONVERTING BIOGAS TO LIQUID FUELS

FIELD OF THE INVENTION

This invention relates to novel and specific methods of producing synthetic liquid hydrocarbon fuels using a mixture of methane and carbon dioxide, typically called biogas. Therefore, the present invention relates generally to the fields of chemistry, chemical engineering, and catalysis.

BACKGROUND

Modern society demands substantial energy and fuel to supply both essential needs and consumer wants. Conventional petroleum and fuel sources have proven to be a volatile resource in terms of international energy dependencies, real and perceived environmental issues, and an unknown limited supply. Alternative sources of suitable fuels has led to a wide variety of efforts such as corn to ethanol processes, biomass to liquid processes, algae to biodiesel processes, and a number of methane conversion processes. Each of these and other current alternatives have both benefits and drawbacks. For example, corn-based fuels have the effect of also detrimentally affecting prices and supply of food sources. There are also debates regarding the net efficiencies of such processes. Biodiesel derived from algae is interesting in that reduced carbon emissions are involved and algae is a renewable resource. However, as with corn-based processes, algae require vast amounts of land to cultivate in practical volumes. Similarly, methane to liquid fuels processes such as the Fischer-Tropsch process have seen commercial use. However, these processes can be difficult to control and often suffer from catalyst deactivation. These processes are also only economical at very large volume scales which require large initial capital investments. Therefore, none of the existing technologies provides scalable, inexpensive and reliable processes for forming hydrocarbon fuels, nor can they be deployed economically at low volume biogas sources.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention and they are, therefore, not to be considered limiting of its scope. It will be readily appreciated that the components of the present invention, as generally described and illustrated in the figures herein, could be arranged, sized, and designed in a wide variety of different configurations. Nonetheless, the invention will be described and explained with additional specificity and detail through the use of the accompanying drawings in which:

FIG. 1 is a flow diagram of a process for producing hydrocarbon fuels in accordance with one embodiment of the present invention.

DETAILED DESCRIPTION OF EXEMPLARY EMBODIMENTS

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout.

Definitions

In describing and claiming the present invention, the following terminology will be used.

The singular forms "a," "an," and "the" include plural referents unless the context clearly dictates otherwise. Thus, for example, reference to "a gas" includes reference to one or more of such materials and reference to "converting" refers to one or more such steps. Furthermore, unless explicitly stated otherwise, reaction steps can be performed sequentially and/or in parallel and can be performed in a common vessel or separate vessels.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

All percentages are provided herein as volume percentages unless otherwise noted. Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Reforming Process

Referring now to FIG. 1, a process for producing a liquid hydrocarbon fuel can begin by obtaining a hydrocarbon-containing gas in a methane production step 10. Although a methane-containing gas can often be productive, other hydrocarbon precursors, including without limitation C1-C4 hydrocarbons such as propane, butane, and ethane, may also be used. The hydrocarbon-containing gas can be synthesized or obtained from a suitable source. The hydrocarbon-containing gas can be produced in any of a number of processes which produce a methane-rich gas having a substantial proportion of carbon dioxide. Suitable processes can include, but are not limited to; anaerobic digestion, fungal decomposition of cellulosic or other plant matter (or, more generally, 'biomass'), or other naturally occurring or man-made phenomena. The source gases for these processes can be from wastewater treatment, sewage treatment, septic tanks, natural gas, biomass conversion (analogous to composting), landfill gas, stranded natural gas, silage decomposition, or the like. In one specific aspect, the hydrocarbon-containing gas can be obtained by anaerobic digestion of organic constituents of municipal wastewater. In one aspect, the hydrocarbon-containing gas can be a biogas, e.g. methane and carbon dioxide as primary components. In another aspect, the hydrocarbon-containing gas can be landfill gas, manure management waste gas, or stranded natural gas.

The digester off-gas or other hydrocarbon-containing gas can be optionally scrubbed in order to reduce impurities such as hydrogen sulfide and organics. Non-limiting examples of suitable scrubbing options can include zinc-oxide adsorbent, molybdenum-cobalt (Mo—Co) conversion of organic sulfur compounds to hydrogen sulfide, iron salt chemical treatment or iron sponge systems. Although actual ppm can range considerably, typical untreated digester gas can have about 200-1000 ppm $H_2S$ depending on the wastewater being treated. In one specific embodiment, scrubbing the hydrocarbon-containing gas can be performed sufficient to remove substantially all $H_2S$. Generally, it can be sufficient to reduce $H_2S$ content to below about 1 ppm, and often in the ppb range using any suitable $H_2S$ abatement technique. Gases having a relatively small amount of $H_2S$ (e.g. about 30-100 ppm) can be treated by single step scrubbing or other processes. For example, a scrubber reactor can be used to absorb $H_2S$ and destroy or remove remnant organics. Although other materials can be useful, Mo—Co can break down organic components, while ZnO can absorb hydrogen sulfides. One alternative material is to use a layered sorbent (e.g. ZnO, Mo—Co, ZnO) to remove $H_2S$, break down thiols and remove generated $H_2S$ in the Mo—Co stage. For example, a Mo/Co system breaks down thiols with the addition of hydrogen and $H_2S$ is removed in the first ZnO step, hydrogen is added in the Mo/Co step and more $H_2S$ is generated. This $H_2S$ is removed during the last ZnO stage. Gases having a larger $H_2S$ content (e.g. greater than about 100 ppm) can be treated by multi-step processes such as iron sponge followed by ZnO bed. Other suitable absorbents or catalysts can include, but are not limited to, a diluted mixture of iron oxide in wood chips and shavings, typically referred to as "iron sponge." The scrubber reactor that contains only ZnO sorbent can be operated at about 1 psig and about 200° C. to about 400° C., with about 200° C. showing particularly good results. By lowering the temperature of the gas (e.g. below about 250° C. and often about 200° C.), the $CO_2$ content can be lowered, although increase sorbent may be desirable.

Regardless of the source, the hydrocarbon-containing gas can generally have a majority of the hydrocarbon source, e.g. greater methane than any other single component. Although other ratios can be suitable, one embodiment includes about 60 vol % methane and about 40 vol % carbon dioxide. The range of methane may generally range from 50-95 vol % with the balance gas comprising or consisting essentially of carbon dioxide. In one aspect, the hydrocarbon-containing gas has about 25% to about 50% carbon dioxide. In another aspect, the hydrocarbon-containing gas has 30% to less than 50% carbon dioxide. Thus, the hydrocarbon-containing gases used herein can use higher carbon dioxide contents than traditional reforming. Although some separation can be performed, in many cases the hydrocarbon-containing gas can be used without removal of carbon dioxide resident in the source gas.

Synthesis gas (an industrially valuable mixture of hydrogen and carbon monoxide) can then be formed from the hydrocarbon-containing gas in a synthesis gas formation step 12. One specific embodiment includes reforming of the hydrocarbon-containing gas with steam to form syngas; other embodiments include without limitation partial oxidation and auto-thermal reforming. The reforming can generally be a composite dry-wet reforming process where both steam and carbon dioxide are present. In one alternative, the reforming process is a tri-reforming process including simultaneous dry reforming, wet reforming and partial oxidation.

The inlet gases can be controlled to produce a synthesis gas having a $H_2$/CO ratio from 0.6 to 2.5 and from about 5 to about 15 vol % $CO_2$. Although not always required, the steam gas can further include oxygen and/or air. Optionally, a small amount of ambient air can be pulled into the reactor sufficient to help balance the heat load of the endothermic reforming reactions. These ratios can be adjusted to balance the heat load in the reactor as well as provide the correct ratio of $CO:H_2:CO_2$ for methanol synthesis. In one aspect, the mixture has a 6:3:1 ratio of hydrogen, carbon monoxide and carbon dioxide. The air can primarily be adjusted to stabilize temperature, and the water content can be used to change the amount of $CO_2$ and increase the $H_2$:CO ratio. Advantageously, increased $CO_2$ can be tolerated, and can even be desirable, without substantial coking at least partially because of the water and by appropriate choice of catalyst as explained in more detail below.

Specific operating parameters can be adjusted, however as a general guideline the reforming can be performed from about 750° C. to about 850° C. and about 0.5 psig to about 30 psig, such as about 800° C. and about 1 psig. Although results can vary, these conditions typically result in about 90% conversion efficiency of methane to carbon monoxide. The reforming can be accomplished using a packed bed reactor, although any device which allows for sufficient gas to catalyst contact surface area can be used. The reforming can typically include a suitable catalyst such as, but not limited to, nickel, iridium, Ru, Rh, Pt, Pd, Co, Fe, Ag, or the like, and combinations or alloys thereof. These catalysts can be unsupported or supported on materials such as γ-alumina, calcium aluminate, regular amorphous alumina, lanthanum oxide, lanthanum aluminate, cesium oxide and specifically, other rare earth metal oxides and can include additives such as rare earth oxides, calcium oxides, and the like. In one specific embodiment, the catalyst can be an alumina-supported catalyst such as a Ni on alumina catalyst. More specifically, the nickel content can be from about 1 wt % to about 10 wt %, such as about 3 wt %. As a general guideline, a low (e.g. less than 10 wt %) Ni content catalyst can process between 30-50% $CO_2$ in a reasonable catalytic lifetime. At lower $CO_2$ concentrations, a higher Ni metal content can be used.

For example, a 3% nickel catalyst can be produced by the incipient wetness technique. A 3% Ni content $Ni(NO_3)_2$ solution in water is first prepared. The amount of water is determined by the weight of the catalyst. Only enough water is used so that the catalyst will substantially completely absorb all of the solution. After the catalyst soaks up the solution, it can be dried in ambient at 900° C. for 10 hours. Before use, the catalyst can be formed in 5% hydrogen balance nitrogen, forming gas at 500° C. for at least 1 hour. The stoichiometry of the catalyst loading, metal percentage and forming gas flow rate will determine the approximate time for reduction to active metallic catalyst. Alternatively, the alumina catalyst can be an Ir on alumina catalyst. Generally, the iridium content can be from about 0.5 to about 3 wt %, such as about 1 wt %. Iridium is more expensive than nickel based materials, but can be cost effective when using smaller scale reactors that require smaller amounts of catalyst load. In one specific aspect, a composite Ni—Ir catalyst can be desirable. One example is a Ni—Ir catalyst having 2.5 wt % Ni and 0.5 wt % Ir with about 0.25 wt % variation for optimization. The Ni—Ir catalysts offer a longer catalyst lifetime over the catalysts that contain Ni only.

The resulting synthesis gas product can be at least partially converted to a methanol product in a methanol synthesis step 14. This methanol synthesis step can generally involve a catalytic reaction. Furthermore, this step can utilize or be based on any number of methanol conversion processes such as, but not limited to, ICI low pressure methanol process, Katalco low pressure methanol process, Lurgi low pressure methanol process, Haldor-Topsoe process, liquid process such as the LPMeOH process, and the like. Suitable catalysts can include copper, zinc oxide, alumina, chromium oxide, and combinations thereof. In one specific embodiment, the catalytic reaction includes a Cu—Zn-Alumina (CZA) as a catalyst in a fixed bed reactor. Particle size of the catalyst can affect available surface area and catalytic activity. Therefore, in one embodiment of the present invention, the methanol synthesis catalyst can have an average particle size of about 20 µm to about 50 µm, although larger particle sizes can be used depending on scaling factors such as space-velocity/pressure drop optimization and the like. The CZA catalyst is typically provided commercially at about 4-8 mm in size. This larger size can be milled to the smaller more suitable sizes for the present invention by ball milling, grinding or other suitable technique. In one specific embodiment, the catalyst further includes bγ-alumina. For example, a particulate mixture can be formed of CZA and γ-alumina. Although conditions can vary, the catalytic process can often be performed at a temperature of about 200° C. to about 300° C., and in one embodiment from about 230° C. to about 240° C. The pressure can also be varied but is often from about 400 psig to about 1000 psig, such as about 600 psig. This methanol synthesis step is typically limited to about 10% conversion of CO to methanol in a packed bed reactor and 60-70% per pass conversion in a liquid-phase process. Thus, the product stream can be optionally recycled either with or without prior removal of the methanol product in order to achieve higher conversion. The product stream can also be converted in reactors in series with interstage product removal for higher conversion as well.

One additional factor that can be manipulated to achieve desirable results for methanol synthesis is the modulus which is defined as $$\frac{[H_2] - [CO_2]}{[CO] - [CO_2]}$$

where [H2], [CO] and [CO2] are respective gas concentrations in the reforming product mixture. In one aspect, the modulus can be 1 to 3, such as 1.5 to about 2.5 and in some cases about 2.5.

A water gas shift reactor can also be used after the reformer to shift the equilibrium of the reformate and remove water from the stream. The water gas shift reaction is: $CO+H_2O \leftarrow \rightarrow H_2+CO_2$. The advantages of using this reactor include: water is removed from the stream, which can harm compression equipment downstream, and hydrogen is produced, which increases the modulus of the reformer outlet stream.

Generally, the methanol product can be converted to the desired hydrocarbon fuel. This can be accomplished by partially converting the methanol product to a dimethyl ether product to form a mixture of methanol and dimethyl ether in a DME synthesis step 16. Optionally, the methanol synthesis from synthesis gas and the DME can be formed concurrently. The DME synthesis can involve a suitable DME catalyst such as, but not limited to, γ-alumina, Cu—Zn-alumina, H-ZSM-5, and combinations thereof. In one specific embodiment, the DME catalyst can consist essentially of γ-alumina and Cu—Zn-alumina catalyst particles, where the γ-alumina is about 5 to about 10 wt % of the DME catalyst. The DME catalyst can be supported or unsupported. In a particulate form, the DME catalyst can generally have a particulate size from about 1 micron to about 1000 micron, and typically from about 10 micron to about 100 micron. The resulting methanol-DME mixture can generally comprise from about 5 vol % to about 50 vol % methanol, and preferably from about 5% to about 10%, with the remainder being DME and typically a small portion of water.

The mixture of methanol and dimethyl ether can be converted to hydrocarbon fuel in a hydrocarbon fuel synthesis step 18. The mixture can be exposed to a ZSM catalyst under conditions sufficient to form the hydrocarbon fuel. The ZSM catalyst can be ZSM-5 having a silicon to aluminum ratio of about 24 to about 30. The catalyst can be supported, unsupported or mixed with an $Al_2O_3$ based binder and extruded to create larger form factor pellets. Furthermore, the catalyst can often have a particle size of about 1 Although conditions can vary, a general guideline for the formation of hydrocarbon fuel is to have a temperature from about 300° C. to about 450° C. and relatively low pressures, e.g. typically about 2 atm up to about 30 atm. Other suitable catalysts may also be used such as, but not limited to, ZSM-11, ZSM-12, ZSM-21, TEA mordenite and the like. The hydrocarbon fuel can vary somewhat in composition, but is often a gasoline mixture of aliphatic hydrocarbons having C5 to C12 chains and aromatic hydrocarbons including xylenes, toluenes, isopentene, and other isoparaffins.

The unrefined hydrocarbon fuel can be used, transported or stored as is, or may be further refined. For example, the hydrocarbon fuel can be fractionated into at least two fractions including light hydrocarbons and heavy hydrocarbons in a fractionation step 20. The heavy fraction can generally include significant portions of durene which can be used or further converted to isodurene.

Each of the synthesis gas formation, methanol synthesis, DME synthesis, and hydrocarbon fuel synthesis steps can generally be performed in separate reactors. However, two or more of these steps can also be performed in a single reactor either sequentially or simultaneously. For example, methanol and dimethyl ether synthesis can be performed in one reactor. In one aspect, the process units can be scaled down to provide a modular system. One advantage of a scaled down modular system is to allow increased reliability and predictability, at least partially due to improved uniformity and monitoring accuracy. The process can be deployed in a self-contained unit about 8 feet wide, 10 feet tall, and 20 to 40 feet long; about the size of a standard shipping container. Such a unit can be located at the source of the hydrocarbon-containing gas and operated in an unmanned fashion at generally less than 5000 gallons per day. The process can be operated in the standalone unit, requiring minimal infrastructure such as a concrete pad and conduit to the hydrocarbon-containing gas and utilities to enable operation. This can also allow the system and process to occur in close proximity to a biogas production source (e.g. within one mile).

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A method of producing a liquid fuel, comprising:
    a) composite wet-dry reforming a hydrocarbon-containing gas containing from 30% to about 50% carbon dioxide with a steam gas to form a mixture of hydrogen, carbon monoxide, and carbon dioxide,
    wherein the forming of the mixture of hydrogen, carbon monoxide, and carbon dioxide does not comprise a partial oxidation reaction;
    b) converting the mixture of hydrogen, carbon monoxide, and carbon dioxide at least partially to a methanol product; and
    c) converting the methanol product to the liquid fuel comprising a gasoline mixture of aliphatic and aromatic hydrocarbons.

2. The method of claim 1, wherein the hydrocarbon-containing gas is obtained by anaerobic digestion.

3. The method of claim 1, further comprising scrubbing the hydrocarbon-containing gas sufficient to remove substantially all $H_2S$.

4. The method of claim 1, wherein the hydrocarbon-containing gas has a majority of methane and 30% to less than 50% carbon dioxide.

5. The method of claim 1, wherein the reforming is performed at about less than 150 psi.

6. The method of claim 1, wherein the reforming is accomplished using a packed bed reactor comprising a supported catalyst.

7. The method of claim 6, wherein the supported catalyst is a Ni—Ir catalyst.

8. The method of claim 7, wherein the Ni—Ir catalyst has 2.5 wt % Ni and 0.5 wt % Ir with about 0.25 wt % variation for each of Ni and Ir.

9. The method of claim 1, wherein the converting the mixture is a catalytic reaction comprising a Cu—Zn-Alumina as a catalyst in a fixed bed reactor.

10. The method of claim 1, wherein the liquid fuel comprises a dimethyl ether product.

11. The method of claim 10, further comprising exposing the dimethyl ether product to a ZSM catalyst under conditions sufficient to form a hydrocarbon fuel.

12. The method of claim 11, wherein the hydrocarbon fuel is a gasoline mixture of aliphatic hydrocarbons having C5 to C12 chains and aromatic hydrocarbons, including xylenes, toluenes, isopentene, and isoparaffins.

13. The method of claim 1, wherein the converting the methanol product comprises a DME catalyst comprising γ-alumina particles.

14. The method of claim 1, wherein the converting the methanol occurs within one mile of a formation source of the hydrocarbon-containing gas.

* * * * *